(12) United States Patent
Parmet et al.

(10) Patent No.: US 10,238,527 B1
(45) Date of Patent: *Mar. 26, 2019

(54) TESTICULAR RETRACTION RESTRAINTS AND METHODS

(71) Applicants: Daniel Edward Parmet, Chicago, IL (US); Lawrence Lanoff, Sedona, AZ (US)

(72) Inventors: Daniel Edward Parmet, Chicago, IL (US); Lawrence Lanoff, Sedona, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/857,586

(22) Filed: Dec. 28, 2017

(51) Int. Cl.
*A61F 5/00* (2006.01)
*A61F 5/41* (2006.01)
*A61H 19/00* (2006.01)

(52) U.S. Cl.
CPC ............ *A61F 5/41* (2013.01); *A61H 19/50* (2013.01); *A61F 2005/414* (2013.01)

(58) Field of Classification Search
CPC ........ A61F 5/41; A61F 2005/411; A61F 5/37; A61H 19/50
USPC ...................................................... 600/38–41
See application file for complete search history.

(56) References Cited

U.S. PATENT DOCUMENTS

| D683,855 S | * | 6/2013 | Magni, Jr. ................... D24/143 |
| 2016/0143767 A1 | * | 5/2016 | Howard ...................... A61F 5/41 600/41 |

* cited by examiner

*Primary Examiner* — John Lacyk
(74) *Attorney, Agent, or Firm* — Law Offices of Jeffrey S. Dixon

(57) ABSTRACT

Described are restraints, and methods of using and making the restraints, for restraining a man's testicular retraction response to sexual stimulation. It is believed that the restraints and methods of use thereby tend to slow or postpone the onset of the man's climax, with the potential to prolong the pleasure of the man and/or his sexual partner. More particularly, clip restraints and loop restraints are described and illustrated. The clip restraints are configured to grip a portion of the scrotum and to present deflection or obstruction features above the reposed positions of each of the man's testicles, configured to deflect or obstruct the movement of the testicles toward a retracted position associated with the onset of the man's sexual climax. Advantageously, clips according to the invention may fold to a narrow thickness, convenient for carrying in a pocket or wallet. Clip members of the restraints may be attracted by magnets, biased by springs, or manually adjusted to a stable gripping position. The loop restraints comprise left-hand and right-hand loops configured to extend around a portion of the scrotum and to define a restraint opening, confining at least a restrained portion of the respective testicle to one side of the restrained opening to limit retraction of the respective testicle through the opening in a direction toward the respective vas deferens.

12 Claims, 12 Drawing Sheets

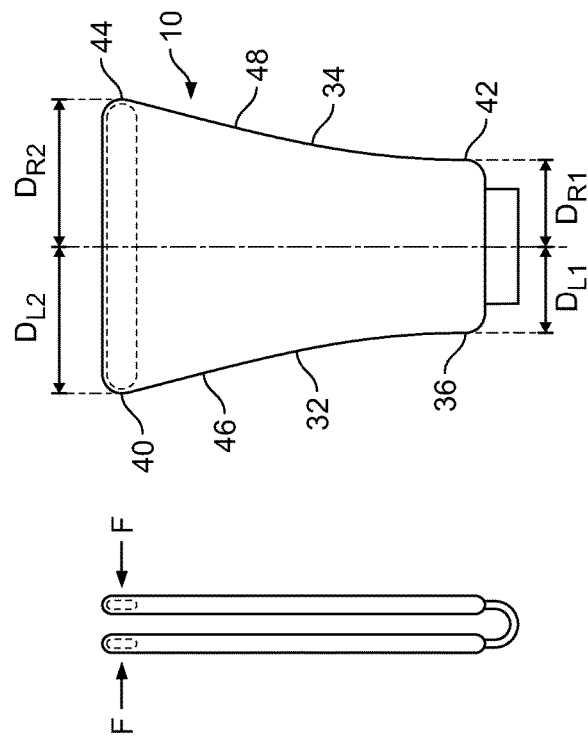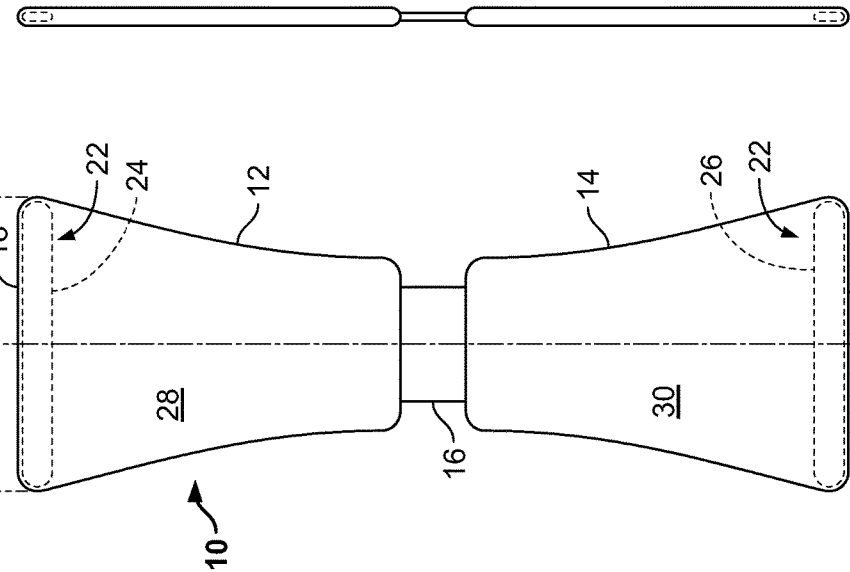

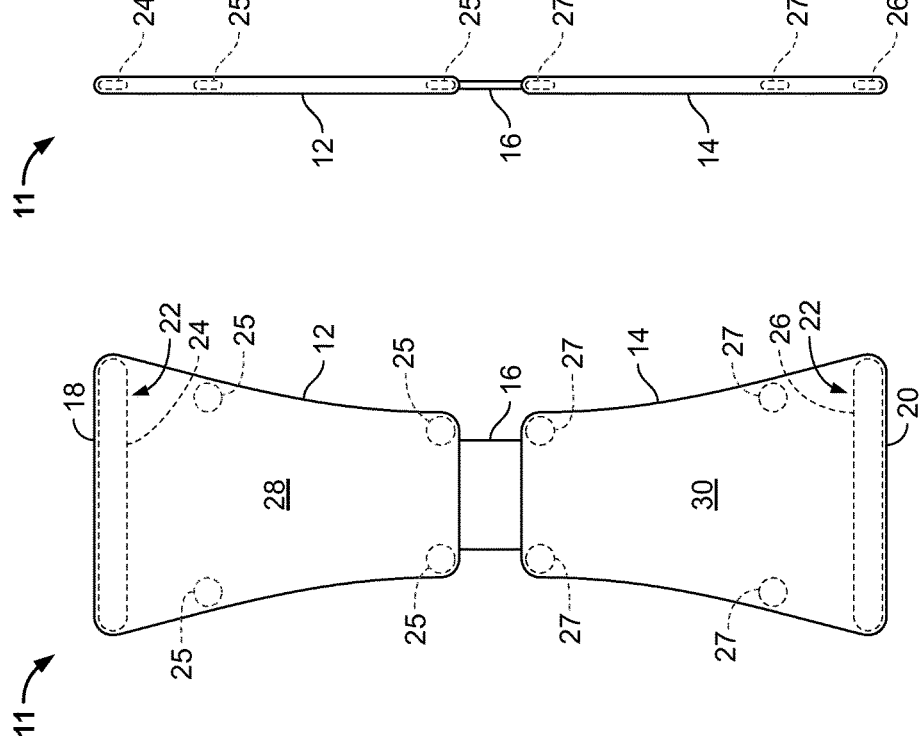
FIG. 5
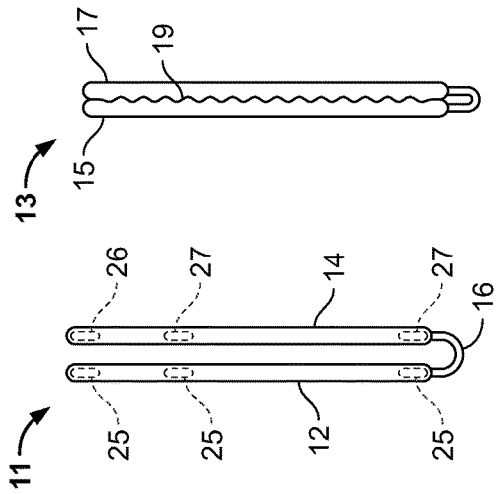
FIG. 6
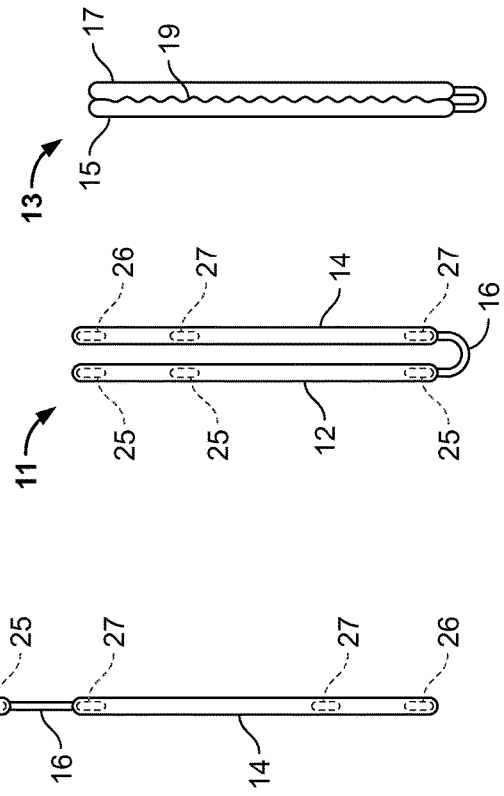
FIG. 7
FIG. 7A

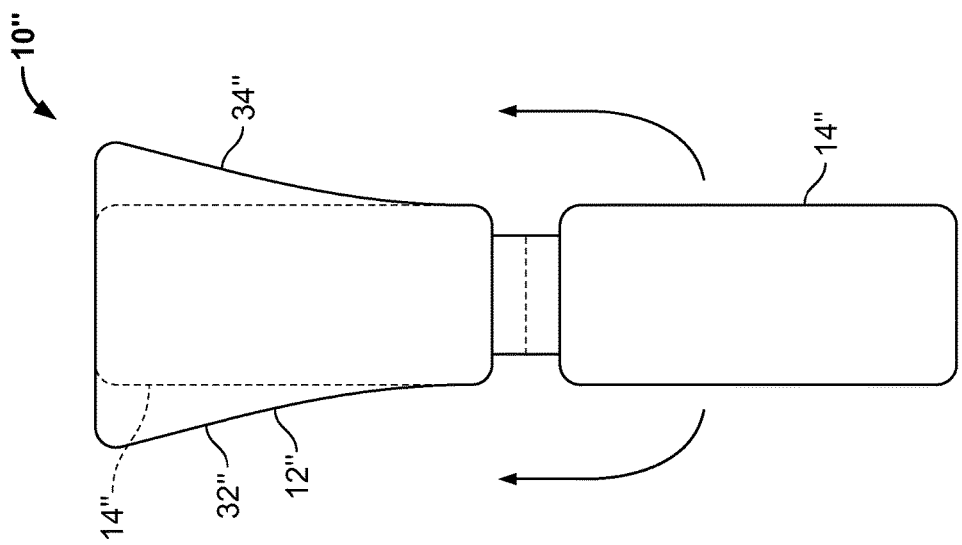
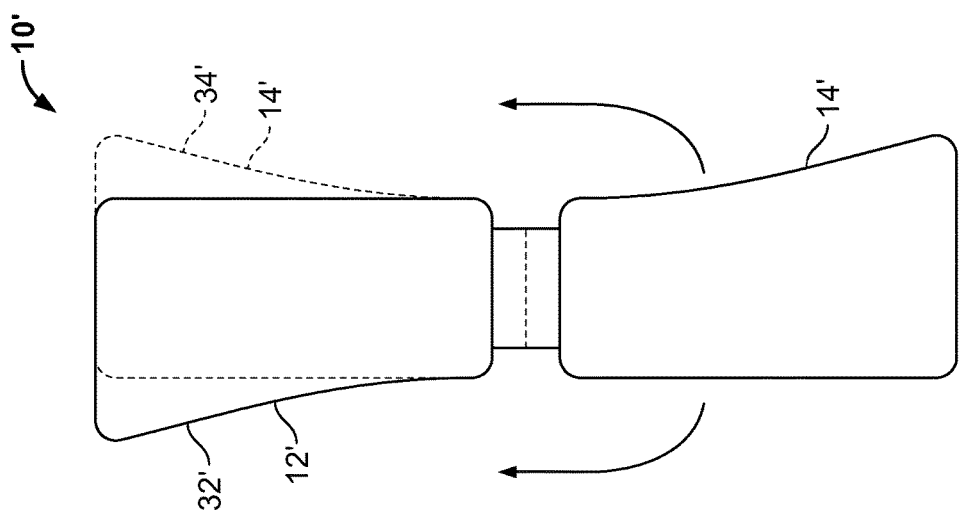

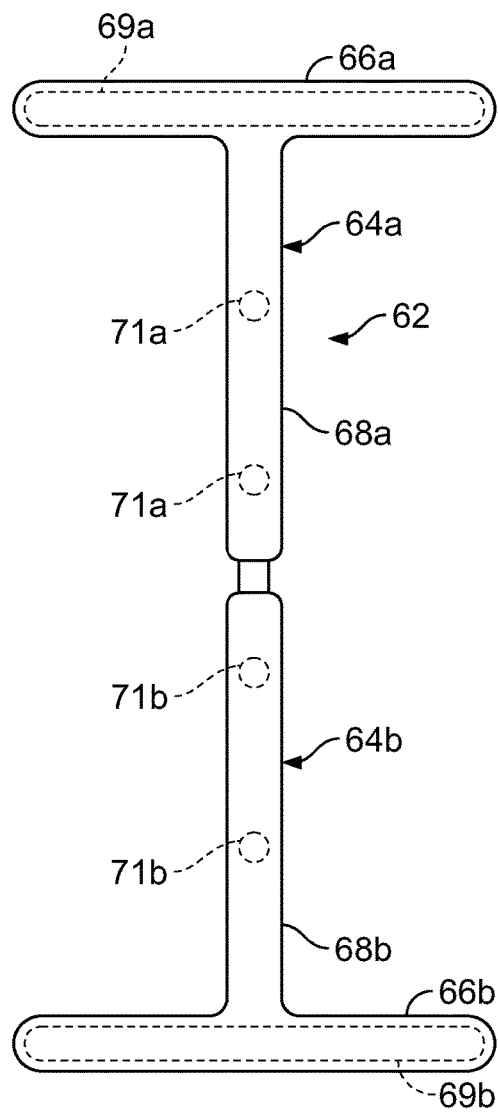
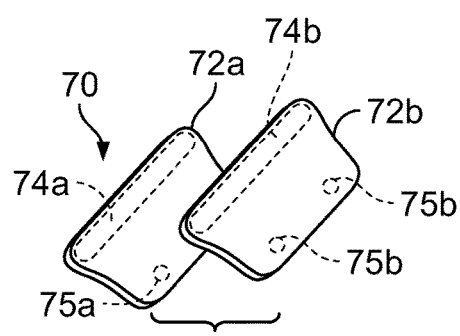
FIG. 13
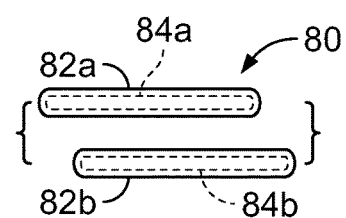
FIG. 14
FIG. 12

TESTICULAR RETRACTION RESTRAINTS AND METHODS

FIELD OF THE INVENTION

The present invention relates to male sexual performance and experience prolonging devices. More particularly, it relates to devices for restraining retraction of the testicles ("restraints") during male sexual stimulation, to delay the onset of the male's sexual climax, and to methods of using and making the restraints.

BACKGROUND

It is well known that the testicles retract inwardly towards the abdomen just prior to or during male sexual climax. Accordingly, male sexual performance may be enhanced or prolonged by restraining such testicular retraction during intimacy. This may benefit a male who desires to prolong the enjoyment of self-stimulation, a male having otherwise short sexual duration compared to his partner, or a male and/or his partner wishing to prolong the enjoyment of sex.

Some existing male anatomy clamping devices may incidentally restrain testicular retraction. However, known devices have shortcomings, such as being unduly restrictive of bodily fluid flow into and out of the testicles and/or penis shaft (many by design), potentially leading to discomfort or physical harm. In addition, existing devices are often cumbersome to don and remove.

A need therefore exists for an improved testicular retraction restraint. Preferably, the restraint should be easy to use, durable, comfortable, small, light, inexpensive to manufacture, and reusable.

SUMMARY OF THE INVENTION

According to aspects of the invention, scrotal clip type and loop type testicular retraction restraints, and methods of making and using them, are provided.

A clip type human testicular retraction restraint according to an aspect of the invention comprises a first clip member configured to be disposed against a first area of a man's scrotum between the testicles; a second clip member configured to be disposed against a second area of the scrotum opposite the first area; and a biasing mechanism configured to produce a gripping force urging the first and second clip members toward each other in a gripping direction to grip a portion of the scrotum between the first and second areas and to suspend the restraint from the gripped portion of the scrotum. The first and second areas of the scrotum may typically be front and rear areas thereof. When the restraint is worn with the portion of the scrotum gripped between the clip members, the restraint presents a right-hand obstructing feature disposed between the man's right testicle and abdomen and a left-hand obstructing feature disposed between the man's left testicle and abdomen. The clip type restraints are configured to grip an area of the scrotum without gripping or surrounding the vas deferens or any part of the testicles themselves, instead restraining the testicles by an obstruction extending obliquely across their path of retraction. The loop type restraints described further below, in contrast, are configured form a loop corresponding to each testicle, to surround (but not compress or constrict) a portion of the vas deferens and/or a portion of a side of the testicle connected to the vas deferens, to define an opening through which the entire testicle cannot pass due to the size and/or shape of the opening.

In an embodiment, the first and second clip members are configured to be interchangeably disposed against either of the first and second areas. Alternatively, each may be configured only to be disposed against a respective one of the first and second areas. For example, the first clip member may have a different shape than the second clip member, each shape being tailored to a respective one of the areas.

In an embodiment, at least one of the clip members includes an upper section configured to engage the man's penis shaft. Such an upper section may simply conform to a lower contour of the penis shaft, or it may include a shaft retention ring extending over at least a portion of a top side of the man's penis shaft. Such a retention ring may be a closed loop, requiring insertion of the tip of the penis, or it may include a gap to facilitate lateral donning at the base of the penis shaft.

In an embodiment, the first and second gripping members are connected at a pivotal joint configured to be disposed approximately at a lower end of the restraint when the restraint is worn. The pivotal joint may, for example, comprise a strip of flexible material or an articulating hinge. Alternatively, where the first and second gripping members are biased together by magnetic attraction, the first and second gripping members need not be connected to each other.

In an embodiment, the first clip member may comprise a first gripping surface configured to be disposed against said first scrotum area, and the second clip member may comprise a second gripping surface configured to be disposed against said second scrotum area. An overlapping region of the first and second gripping surfaces thus defines a gripping area, the size of which may, for example, be in a range from about 2 in$^2$ to about 7 in$^2$.

In an embodiment, each of the first and second clip members has a thickness in the gripping direction no greater than about ¼ inch.

In an embodiment, the combined thickness of the clip members in the gripping direction is no greater than about ½ inch, however divided between the two.

In an embodiment, a profile of the restraint in a plane normal to the gripping direction may lie within an approximately 3.5-in by 2-in rectangle.

Advantageously, compact dimensions such as the foregoing may permit the device to be easily carried, such as in a pocket, wallet, or purse.

In an embodiment, the right-hand obstructing feature comprises at least a portion of a right side of at least one of the first and second clip members that tapers to the right toward an upper end of the right side, and the left-hand obstructing feature comprising at least a portion of the left side of at least one of the first and second clip members that tapers to the left toward an upper end of the left side.

In an embodiment, the biasing mechanism comprises a magnet carried by at least one of the first and second clip members, and a magnetically attracted component carried by the other clip member. A "magnetically attracted component" may be, but need not be, another magnet.

An embodiment further comprises an engaging surface of at least one of the first and second clip members being configured to resist downward sliding of the engaging surface against the respective first or second area of the man's scrotum. The engaging surface may, for example, be composed of a high-friction material, or it may comprise one or more surface ribs oriented generally horizontally when the restraint is worn. Both clip members may comprise such ribs, and the ribs may be configured to interdigitate when the clip closes to limit its closed thickness.

In a method of manufacturing a clip type restraint according to an aspect of the invention, the elements of any embodiment described above may be formed and combined to form the restraint in a suitable manner. Suitable materials may be selected, as described in more detail elsewhere. Where magnetic components are included in the clip members, the magnetic components may be overmolded, hemmed, encased, fastened, adhered, or otherwise appropriately attached.

In a method of restraining human testicular retraction according to an aspect of the invention, using a restraint as in any above described embodiment, a portion of the man's scrotum generally disposed between the left and right testicles is positioned between the first and second clip members, and the gripping force is applied to urge the clip members together to grip the portion of the man's scrotum between the clip members.

A loop-type human testicular retraction restraint according to an aspect of the invention comprises a left-hand loop defining a left-hand opening through which an entire left testicle is unable to pass, and a right-hand loop defining a right-hand opening through which an entire right testicle is unable to pass. The left-hand loop is configured to be worn around a left-hand section of a scrotum with the left-hand opening disposed between at least a restrained portion of a left testicle and at least a portion of a corresponding left vas deferens, thus restraining passage of the restrained portion of the left testicle through the left-hand opening toward the left vas deferens. Likewise, the right-hand loop is configured to be worn around a right-hand section of a man's scrotum with the right-hand opening disposed between at least a restrained portion of a right testicle and at least a portion of a corresponding right vas deferens, thus restraining passage of the restrained portion of the right testicle through the right-hand opening toward the right vas deferens.

In an embodiment, the left-hand loop is connected to the right-hand loop to maintain a fixed distance between the left-hand opening and the right-hand opening. That is, the restraint should be stiff enough in the dimension extending between the left-hand and right-hand openings to prevent appreciable reduction of the distance between the openings, even when worn during vigorous intercourse.

In an embodiment, each of the left-hand loop and right-hand loop is manually openable and closable. For example, each of the left-hand loop and right-hand loop may comprise a flexible member having spaced apart closure portions manually movable into and away from proximity, the closure portions being manually attachable to close the respective loop and manually detachable to open the respective loop. Such closure portions may, for example, be snaps, hook-and-loop fasteners, or magnetic couplings. A "magnetic coupling" will be understood to be a pair of bodies attracted to each other by a magnetic force, at least one of which is a magnet.

A method of restraining human testicular retraction, according to an aspect of the invention, uses a loop-type restraint substantially as described above. The method comprises, prior to a man's sexual climax, donning the left-hand loop around the left-hand section of the man's scrotum, and donning the right-hand loop around the right-hand section of the man's scrotum.

BRIEF DESCRIPTION OF THE DRAWINGS

FIG. 1 is a front elevation view of a scrotal clip according to an aspect of the invention, in an open state.

FIG. 2 is a side elevation view of the scrotal clip of FIG. 1, in an open state.

FIG. 3 is a side elevation view of the scrotal clip of FIG. 1, in a closed state.

FIG. 4 is a front elevation view of the scrotal clip of FIG. 1, in a closed state.

FIG. 5 is a front elevation view of a scrotal clip according to an aspect of the invention, in an open state.

FIG. 6 is a side elevation view of the scrotal clip of FIG. 5, in an open state.

FIG. 7 is a side elevation view of the scrotal clip of FIG. 5, in a closed state.

FIG. 7a is a side elevation view of a scrotal clip according to an aspect of the invention, in a closed state.

FIG. 9a is a front elevation view of a scrotal clip according to an aspect of the invention.

FIG. 9b is a front elevation view of a scrotal clip according to an aspect of the invention.

FIG. 12 is a front elevation view of a scrotal clip according to an aspect of the invention.

FIG. 13 is a front elevation view of a scrotal clip according to an aspect of the invention.

FIG. 14 is a front elevation view of a scrotal clip according to an aspect of the invention.

DETAILED DESCRIPTION OF THE INVENTION

Described in this section and illustrated in the accompanying drawings are exemplary embodiments of testicular retraction restraint according to aspects of the invention. The restraints are illustrated in some embodiments as scrotum-gripping clips with left-hand and right-hand features configured to deflect or obstruct retracting movement of the testicles. The clips apply direct pressure to grip and frictionally adhere to a central region of the scrotum, without gripping or surrounding any portion of a testicle or vas deferens. In other embodiments, the restraints are illustrated as closable loop restraints. The loop restraints comprise a pair of loops, each loop having a flap or flaps fastened to surround a portion of the scrotum disposed between the respective testicle (or its widest section) and the abdomen. An inner edge of the loop, defining an opening, is sized and/or shaped to block passage of the testicle, or at least a restrained portion of the testicle, from passing through the opening in the direction of the retraction response to sexual stimulation, that is, a direction generally following the vas deferens medially and/or upwardly into the abdomen.

Scrotal Clip Embodiments

Figure 8:
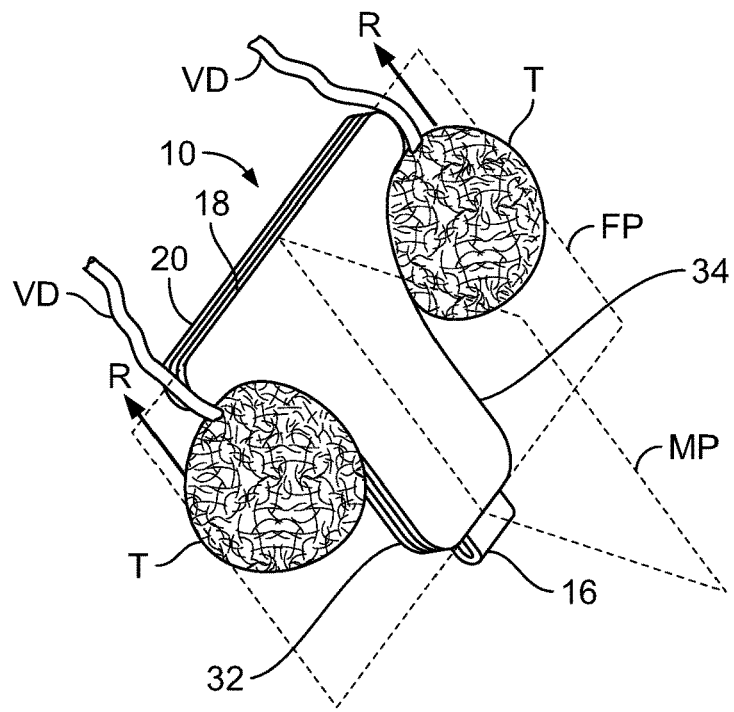
FIG. 8 is a perspective view of the scrotal clip of FIG. 1, depicted in a manner of wearing the clip, with the scrotum removed to reveal a position of the clip in relation to the testicles and vas deferens.

With reference to FIGS. 1-4, 8, and 9, scrotal clip 10 comprises an integral body including a first clip member 12 and a second clip member 14 movably connected to first clip member 12 at a connecting portion 16. First and second clip members 12, 14 include respective free ends 18, 20 distant from connecting portion 16. A biasing mechanism 22, illustrated for scrotal clip 10 as mutually attracted magnetic elements 24, 26 retained in respective clip members 12, 14, is configured to draw opposed first and second gripping faces 28, 30 of first and second clip members 12, 14 towards each other to produce a gripping force F therebetween. Magnetic elements 24, 26 are depicted as laterally elongate strips positioned near respective free ends 18, 20, but other configurations are possible within the scope of the invention, such as in a clip 11 described below. Clip 10 is thus configured to grip a portion of the scrotum between the testicles T, as best seen in FIG. 8. The gripped area of the scrotum lies approximately in a frontal plane FP bisecting each testicle T.

A clip 11 depicted in FIGS. 5-7 is similar to clip 10, with the addition of a respective plurality of magnetic elements 25, 27 arranged near the respective side edges of clip members 12, 14, to provide a more uniformly distributed gripping force.

A clip 13 depicted in FIG. 7a is also similar to clip 10, with the opposed surfaces of its respective clip members 15, 17 including a slip-resistant feature, illustrated as horizontally aligned gripping ribs 19. Ribs 19 may be configured to interdigitate when clip 13 is folded, rather than meeting peak-to-peak, to minimize a folded thickness of clip 13. In lieu of gripping ribs, the opposed surfaces of clip members according to the invention may instead be composed of a high-friction material, with the same object of enhancing the resistance of the clip to downward slippage in use.

Figure 9:
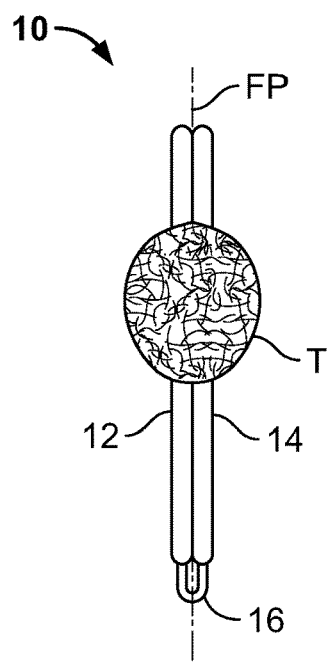
FIG. 9 is a side elevation view of the scrotal clip worn in the manner shown in FIG. 8, depicted in relation to a testicle.

When clip 10 is worn in the manner illustrated in FIGS. 8 and 9, a left side edge 32 and a right side edge 34 of clip 10 each exhibit an outward taper in an upward direction toward the male's abdomen. The outward taper of left side edge 32 and right side edge 34 results in a camming or wedging profile that tends to deflect the testicles T laterally outwardly as they are drawn upwardly in directions R by the male's sexual response, while at the same time avoiding the pinching of vas deferens VD. It is believed that restraining movement of the testicles to or toward a fully retracted position in the groin or abdomen in this manner tends to delay the male's climax and prolong his sexual endurance. This in turn improves his enjoyment of self-stimulation or sex as well as prolonging his partner's sexual pleasure and increasing his partner's likelihood of reaching climax.

A left side edge and right side edge of a clip according to the invention may each be defined by aligned, overlapping lateral portions of each of two congruently shaped clip members, as in clip 10. In another embodiment illustrated in FIG. 9a, a left side edge 32' of clip 10' comprises only a portion of a first clip member 12', and a right side edge 34' of a clip 10' (shown in dashed lines indicating a folded position of a second clip member 14') comprises only a portion of a second clip member 14', so that each clip member 12', 14' serves to deflect only the respective right or left testicle. In still another embodiment of a clip 10" illustrated in FIG. 9b, a first clip member 12" defines both side edges 32", 34", and neither side edge 32", 34" comprises any portion of a second clip member 14".

The respective tapers of a left side edge and right side edge of a testicular retraction restraint according to the invention can be characterized in part by distances between a restraint axis (that is, an axis of the restraint configured to approximately align vertically with a midplane MP of the scrotum when worn, with reference to FIGS. 8 and 9) and certain points on the respective edge, such as the nearest and farthest points from the axis on the respective edge (or on an operative portion of the respective edge that is configured to engage the testicle to deflect, limit, or restrain its retracting movement). For example, with reference to FIGS. 1 and 3, clip 10 exhibits a taper in which a left side edge lower endpoint 36 lies at a transverse distance $D_{L1}$ from a clip axis 38, a left side edge upper endpoint 40 lies at a transverse distance $D_{L2}$ from clip axis 38, a right side edge lower endpoint 42 lies at a transverse distance $D_{R1}$ from clip axis 38, and a right side edge upper endpoint 44 lies at a transverse distance $D_{R2}$ from clip axis 38. It will be understood that the "upper endpoint" and "lower endpoint" of an operative portion of a side edge of a restraint according to the invention need not correspond to an uppermost portion of the restraint itself, or even of the entire side edge, but only of the operative portion referred to thereof, although any portion of the restraint that extends above the side edge upper endpoints should not impede placement of the restraint so that the upper endpoints are positioned above the testicles in partially retracted or un-retracted repose. Likewise, a "lower endpoint" of a side edge need not correspond to a narrowest point, nor an "upper endpoint" to a widest point of the operative portion.

The profile of clips 10, 10', 10" is illustrated as symmetrical or approximately symmetrical about midplane MP when worn (for example, symmetrical within about +/−0.1 in.), such that $D_{L1}$ and $D_{R1}$ are at least approximately equal, and $D_{L2}$ and $D_{R2}$ are at least approximately equal. In one embodiment, $D_{L1}$ and $D_{R1}$ are about 0.65 in., while $D_{L2}$ and $D_{R2}$ are about 1.2 in, and the respective left and right side edges 32, 34 follow a gentle curved path between their respective endpoints, having a minor (such as a minimum or local minimum) radius of curvature at respective saddle points 46 and 48, which may, for example, be shaped to approximately accommodate the curvature of each testicle. For a typical or average male anatomy, this profile shape of clips 10, 10', 10" is believed to be effective to restrain the retracting movement of the testicles as they are pulled generally upward towards the abdomen by a muscle response stimulated by the male's impending sexual climax, so as to prevent a positioning of either testicle that would otherwise tend to trigger an immediate or accelerated climax, or contribute to its onset. In the case of clip 10, the desired effect is achieved at least in part by upper endpoints 40, 44 lying at a sufficient distance from axis 38 to impede their retracting movement. At the same time, the positions of lower endpoints 36, 42 allowing for the testicles to repose in comfortable proximity to each other, when not retracted, or when retracted only partially to the extent permitted by clip 10.

Figure 10:
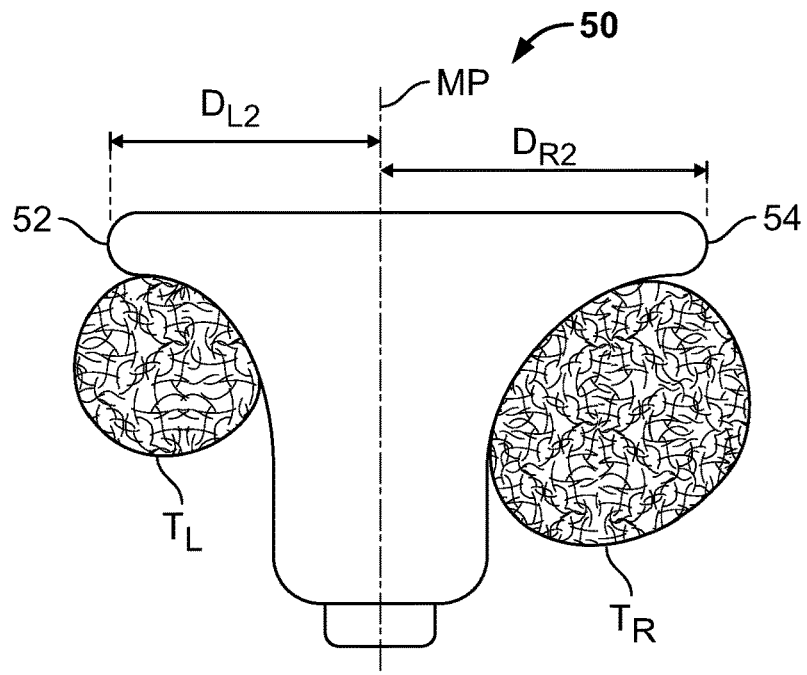
FIG. 10 is a front elevation view of a scrotal clip according to an aspect of the invention, depicted in a manner of wearing the clip, with the scrotum removed to reveal a position of the clip in relation to the testicles.

Clips 10, 10', 10" described above include differently shaped clip members, but exhibit the same frontal profile shape in a closed, gripping position. Other embodiments of a restraint according to the invention may have significantly different frontal profile shapes. For example, a restraint may be configured to exhibit an asymmetrical profile about midplane MP, for example, as in a clip 50 depicted in FIG. 10, wherein distances $D_{L2}$, $D_{R2}$ of a respective upper left side edge endpoint 52 and upper right side edge endpoint 54 from midplane MP are unequal. Such an asymmetrical shape may advantageously accommodate a male's anatomical asymmetry, such as when a left testicle $T_L$ and a right testicle $T_R$ are of different sizes and/or shapes or tend to repose in or retract to different positions, or when other constraints on the movement of the testicles toward or into the groin or abdominal cavity from the scrotum, such as the shape of neighboring anatomical structures or other physiological factors, have an overall asymmetrical effect.

Figure 11:
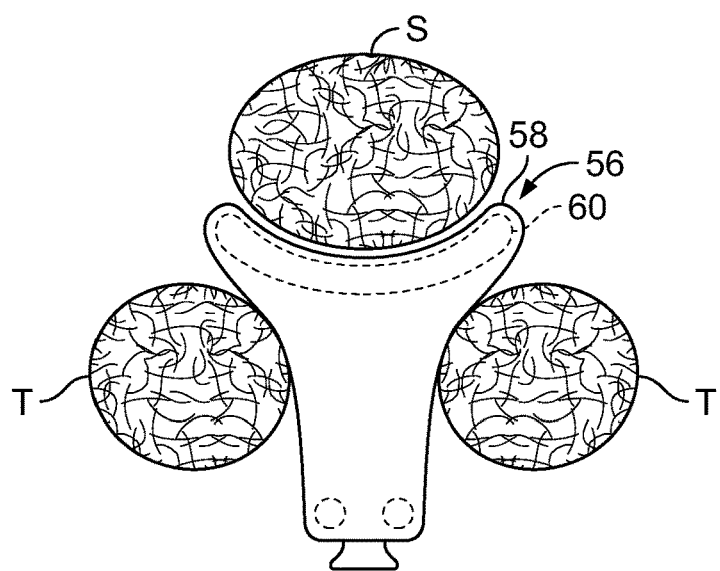
FIG. 11 is a front elevation view of a scrotal clip according to an aspect of the invention, depicted in a manner of wearing the clip, with the scrotum removed to reveal a position of the clip in relation to the testicles and a cross section of the penis shaft.

Still other alternative restraint profile shapes are illustrated in FIGS. 11 and 12. A clip 56 shown in FIG. 11 in a closed position includes a concave curved upper edge 58 to conform to a lower portion of a penis shaft S. A magnetic element 60 of clip 56 may optionally be curved to conform to curved upper edge 58.

Another clip 62 shown in FIG. 12 includes T-shaped clip members 64a, 64b with respective thin horizontal segments 66a, 66b and thin vertical segments 68a, 68b, respective elongate magnetic elements 69a, 69b, and respective round magnetic elements 71a, 71b. The thin aspect of vertical segments 68a, 68b may advantageously minimize impingement on the testicles in repose or in a partially retracted state. On the other hand, drawbacks of thin vertical segments 68a, 68b may include reduced frictional retention of the restraint in a desired position when worn and/or reduced structural integrity, potentially leading to stress concentrations and stretching or tearing. Clip 62 may also be less effective at delaying male sexual climax than another clip type restraint, such as clip 10, 10', 10", 11, 13, 50, or 56, whose tapered region is configured to deflect a retracting movement of the testicles at a lower position, thus corresponding to an earlier stage of sexual response.

Illustrated in FIGS. 13 and 14 are two alternative two-piece embodiments of a testicular retraction restraining clip according to the invention. A clip 70 shown in FIG. 13 includes clip members 72a, 72b that are fully separate and configured to be drawn together by the attraction of respective elongate magnetic elements 74a, 74b and respective round magnetic elements 75a, 75b. Clip members 72a, 72b include respective tapered side edges 76a, 76b and 78a, 78b, which are similar to an upper portion of tapered side edges 32, 34 of clip 10, whereas a lower portion of each clip member is omitted. The resulting material savings are a cost benefit permitted by a two-piece clip obviating the need for clip members 72a, 72b to extend to a connecting portion configured to be positioned below the scrotum. Shown in FIG. 14 is a still further reduced embodiment of the invention as a two-piece clip 80, including separate elongate clip members 82a, 82b drawn together by respective magnets 84a, 84b. A trade-off of the two-piece clips shown in FIGS. 13 and 14 is that the lack of a connecting portion may make aligning the members at the front and rear sides of the scrotum more cumbersome, as well as likely precluding one-handed application of either of clips 70, 80.

Figure 15:
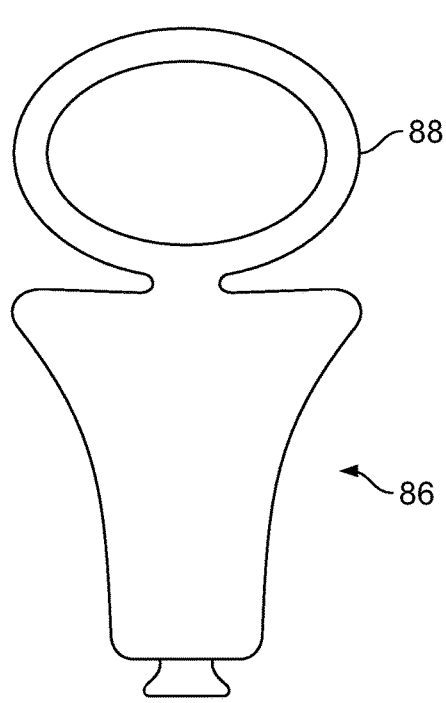
FIG. 15 is a front elevation view of a scrotal clip according to an aspect of the invention, depicted in a closed state.
Figure 16:
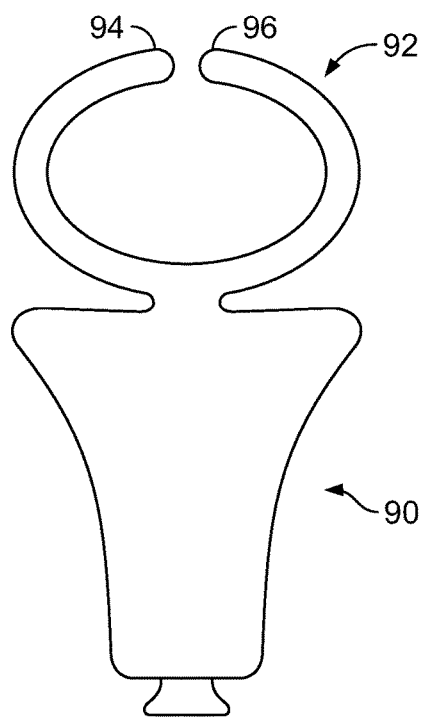
FIG. 16 is a front elevation view of a scrotal clip according to an aspect of the invention, depicted in a closed state.

Illustrated in FIGS. 15 and 16 are two more alternative embodiments of the invention configured with penis shaft retention features, which may help to anchor and stabilize the clip members. Accordingly, a clip 86 shown in FIG. 15 includes a closed loop shaft retention ring 88 configured to slide over the tip of the penis shaft to its base, while a clip 90 shown in FIG. 16 includes an open-loop shaft retention ring 92 having left and right flexible elastic curved members 94, 96, which are sufficiently elastic to be pulled apart around the base of a penis shaft and to return to their relaxed positions to retain the penis shaft once released. It will be understood that neither closed loop retention ring 88 of clip 86 nor open loop retention ring 92 of clip 90 need apply tight pressure, such as would constrict fluid flow. However, should such constriction be desired in addition to restraining testicular retraction, either of rings 88, 92 may be made with the appropriate size and elasticity to achieve it.

Figure 17:
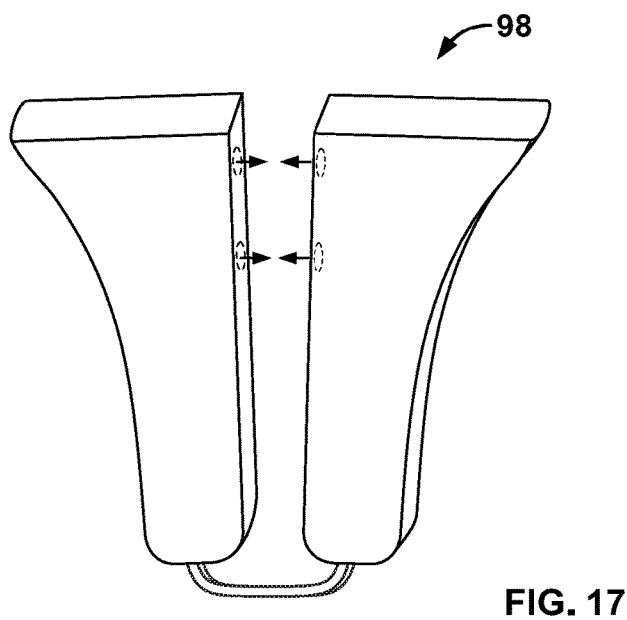
FIG. 17 is a front perspective view of a laterally gripping scrotal clip according to an aspect of the invention, depicted in a partially closed state.

Depicted in FIG. 17 is yet another embodiment of the invention as a clip 98 that is configured to close laterally, gripping a portion of the scrotum approximately at a midplane thereof. While midplane application of clip 98 may be more awkward than the frontal plane application of the clips described above, a benefit is that accidentally pinching or constricting the vas deferens of either testicle would be nearly impossible.

In addition, biasing elements other than magnets may be used within the scope of the invention to draw a pair of appropriately sized and shaped clip members together. For example, an alternative category of biasing mechanisms within the scope of the invention includes those configured to transmit a gripping force through a mechanical load path bypassing the male's scrotal tissue, such as below the scrotum at the approximate location of connecting portion 16 of clip 10 when worn, instead of by directing a magnetic field through the scrotum. Absent magnetic attraction, it will be understood that the gripping members of a restraint would require a certain degree of bending resistance (stiffness) to effectively transmit a mechanical gripping force to a gripped area of the scrotum held between them.

Figure 20:
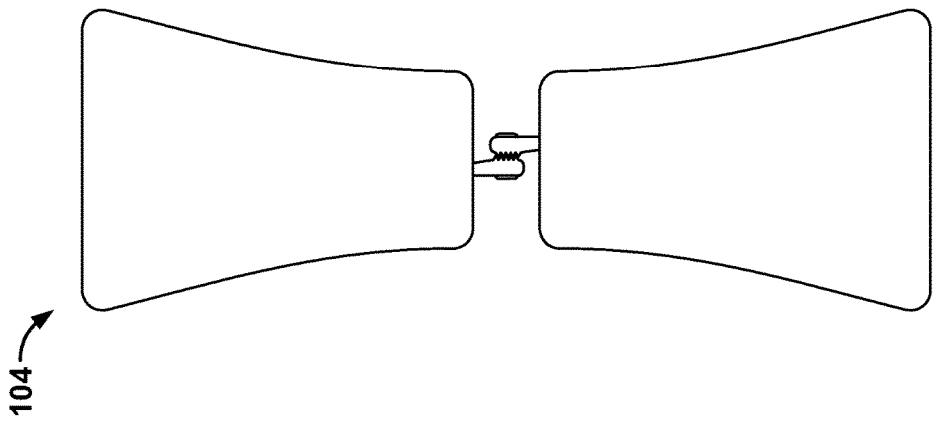
FIG. 20 is a front elevation view of an interdigital locking collar scrotal clip according to an aspect of the invention.
Figure 19:
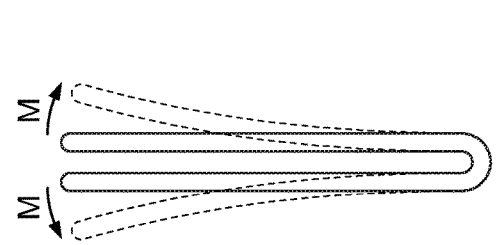
FIG. 19 is a side elevation view of a bending flexion scrotal clip according to an aspect of the invention.
Figure 18:
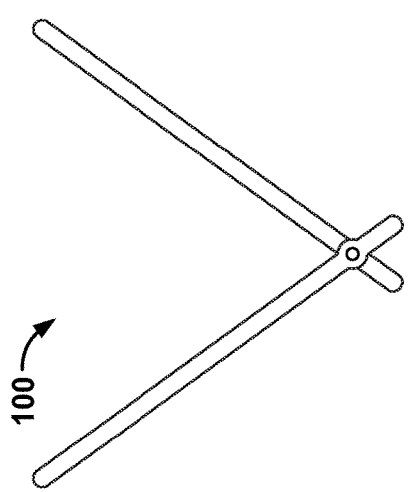
FIG. 18 is a side elevation view of a spring-biased scrotal clip according to an aspect of the invention.
Figure 21:
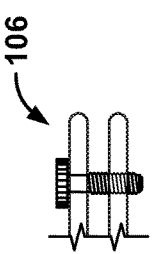
FIG. 21 is a rotated, truncated side view of a self-locking screw adjustment scrotal clip according to an aspect of the invention.

A mechanical gripping force may be produced by a biasing element or applied manually in conjunction with locking or restraining the relative positions of the clip members. For example, a separate pivotal or linear spring component may connect the two clip members and be configured to be disposed below the scrotum, as in a clip 100 shown in FIG. 18 (pivotal spring illustrated). An alternative biasing element may comprise one or both clip members themselves, or an elastically bending portion thereof, as in a bending flexion clip 102 whose clip members are configured to flex under a manually applied bending moment M, distributing a bending strain along a length of each member, and return to a relaxed or preloaded gripping state when moment M is released, as shown in FIG. 19. If the gripping force is instead manually applied, a suitable locking (or restraining) mechanism could be an interdigital collar, as in a clip 104 shown in FIG. 20, a frictional or interdigital sliding joint (not shown), or a self-locking screw adjustment mechanism, as in a clip 106 (truncated) shown in FIG. 21. In still another embodiment not shown, the clip members may be connected by a plastically deformable joint, such as one or more bendable stiff wires, which tends to resist deformation, but once deformed, to retain its deformed state and resist further deformation, including return to its initial state. In each case, as for the one-piece magnetic gripping embodiments described in more detail above, mechanical connections between the clip members are preferably configured to be located below the scrotum, so as to avoid the need for opposed portions of the restraint to straddle the vas deferens, possibly resulting in pinching thereof, or requiring a built-in clearance to avoid pinching.

A variety of materials may be suitable for constructing testicular retraction restraint clips according to the invention. For example, clip members and connecting portions may be formed from a polymer (e.g., silicone or other suitable elastomer), leather, lightweight metal, wood, or fabric material, or any other material that can be comfortably held against the skin of the scrotum and can be used to form a clip of appropriate dimensions that is sufficiently durable and lightweight. Each coordinating pair of magnetic elements may include two magnets or one magnet and a corresponding magnetically attracted body. Suitable magnets include rare-earth magnets, whose high strength and light density render them advantageous for a restraint that must grip tightly enough to produce sufficient traction against the scrotum to frictionally support its own weight suspended therefrom. Magnetic elements according to the invention may be retained in their respective clip members by any suitable means, such as over-molding (in the case of polymeric clip members), adhesive bonding, or hemming/stitching.

Loop Restraint Embodiments

With reference to FIGS. 22-30, embodiments of the invention as a loop restraint will now be described in detail. The illustrated loop restraints comprise a broad and thin body of flexible material having a left side and a right side, each side including a respective closure configured to removably attach two spaced-apart attachment portions of the respective side. Illustrated examples of the attachment portions include magnetic connectors and snaps. Hook-and-loop fasteners (such as Velcro® hook-and-loop fasteners) may alternatively be employed. When the attachment portions come together, the respective side of the loop restraint body forms a restraining loop defining a restraining opening sized and shaped to prevent passage of a testicle through the restraining opening. More particularly, when the restraint is worn, each testicle should be confined to a generally lateral and/or lower side of its respective restraining opening, thus limiting generally medial and/or upward retracting movement of the respective testicle toward the male's abdominal cavity. The restraining opening preferably has an area sized and/or shaped to prevent the testicle from passing fully through the opening, regardless of whether the testicle is stationary or in gyrating motion typical of sexual intercourse, or whether the male's testicular retraction response to sexual stimulation or impending climax is engaged or triggered.

Figure 22:
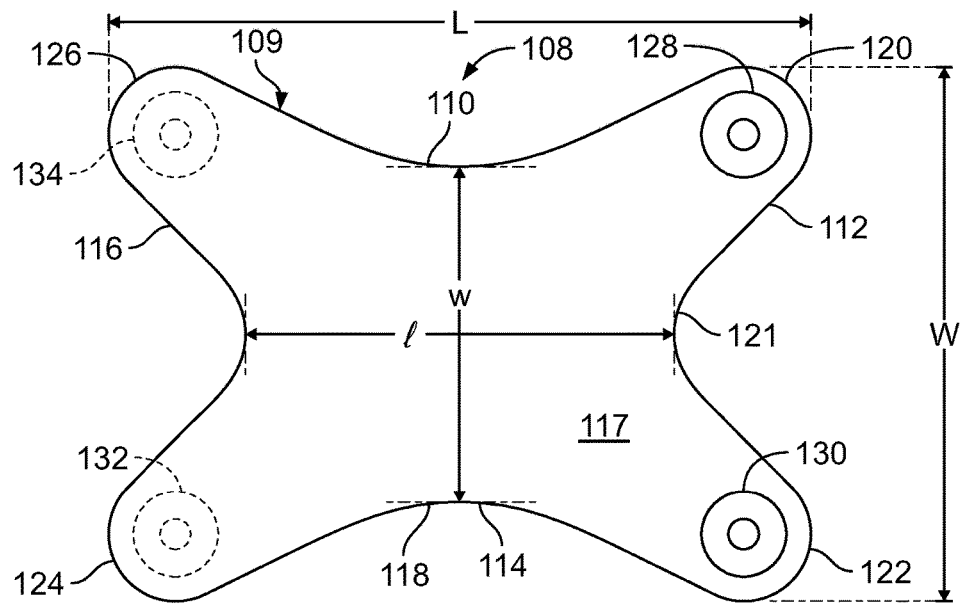
FIG. 22 is a top plan view of a scrotal loop restraint according to an aspect of the invention.

Turning to FIGS. 22-25, a loop restraint embodiment of the invention is illustrated as a loop restraint 108 having a broad and thin flexible body 109 with a left side 110, a front side 112, a right side 114, a rear side 116, an inner face 117, and an outer face 119. Each side 110-116 of body 109 has a predominantly concave contour, so that a minor width w (which may, for example, be a minimum or local minimum width) of body 109 occurs generally at a lateral midsection 118 thereof, and so as to define outwardly flared flaps at each corner where adjacent sides meet, namely, a front-left flap 120, a front-right flap 122, a rear-right flap 124, and a rear-left flap 126. A major width W (which may, for example, be a maximum or local maximum width) occurs generally at lateral extremes of front flaps 120, 122, as depicted in FIG. 22, and/or of rear flaps 124, 126. In this regard, it is to be understood that, while the profile of body 109 is typically symmetrical about an anteroposterior longitudinal axis, except in customized or alternative forms to accommodate varying degrees of anatomical asymmetry observed in the male population, front-to-rear asymmetry may be standard in a loop restraint according to the invention, as so that a major width of a front portion of a given restraint may be significantly different from that of a rear portion thereof, as seen in the variations of loop restraint embodiments illustrated in FIGS. 26-30.) Similarly, a minor length l of body 109 occurs generally at a longitudinal midsection 121 thereof, while a major length L of body 109 occurs generally at longitudinal extremes of left flaps 120, 126, as depicted in FIG. 22, and/or of right flaps 122, 124. Longitudinal midsection 121 may also be referred to as a "connecting portion" of body 109, which joins a left-hand loop, comprising left flaps 120, 126 and a band of material extending between them along left side 110, to a right-hand loop, comprising right flaps 122, 124 and a band of material extending between them along right side 114. This connecting region plays a significant role in maintaining a separation distance between testicles T, as described in more detail below.

Each flap bears a corresponding snap, namely, a front-left female snap 128, a front-right female snap 130, a rear-right male snap 132, and a rear-left male snap 134. It is to be understood that the positions of male and female snaps on either or both sides of a loop restraint according to the invention may be reversed from front to rear. However, it is preferred that male snaps be disposed on the outer face and female snaps on the inner face. While it is possible to provide both snaps on the same face, snapping inner faces together would increase the likelihood of pinching skin in the snap, while snapping outer faces together would position a tail portion of each flap inside the loop, potentially applying uncomfortable uneven pressure on a testicle within the loop.

Figure 23:
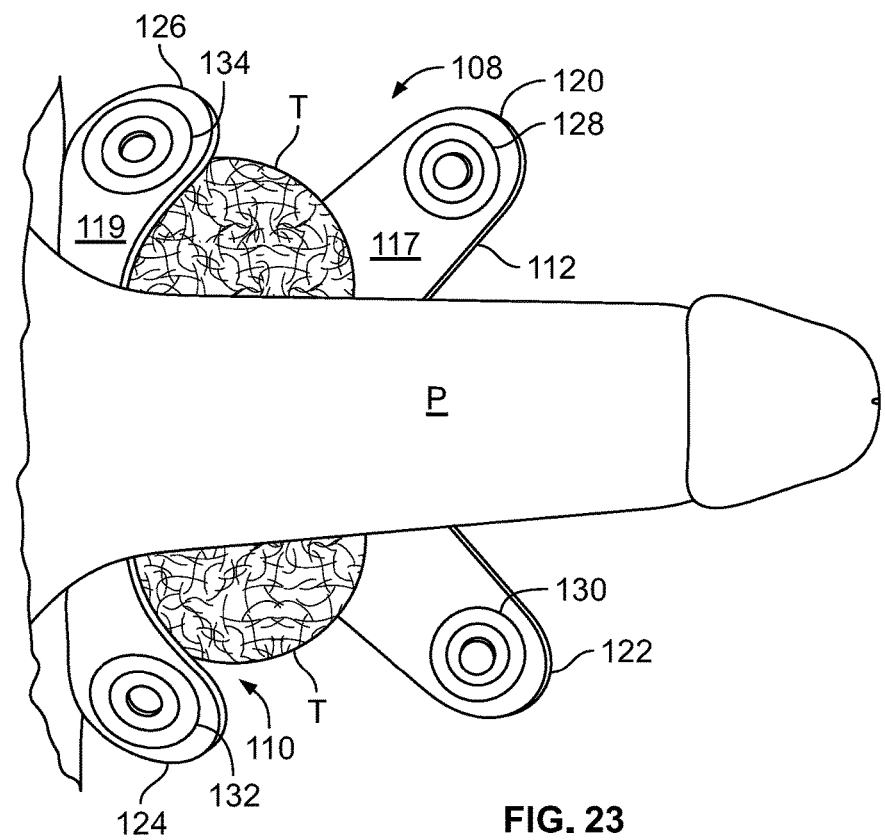
FIG. 23 is a top plan view of the scrotal loop restraint of FIG. 22, illustrating part of a method of donning the restraint.
Figure 24:
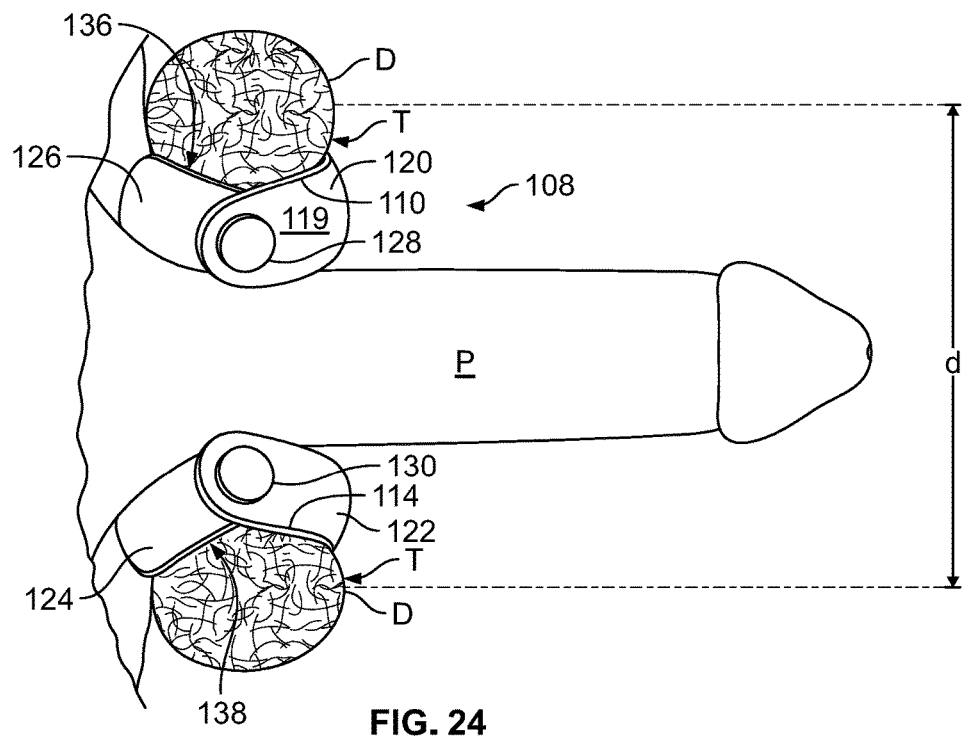
FIG. 24 is a top plan view of the scrotal loop restraint of FIG. 22 in a donned state.
Figure 25:
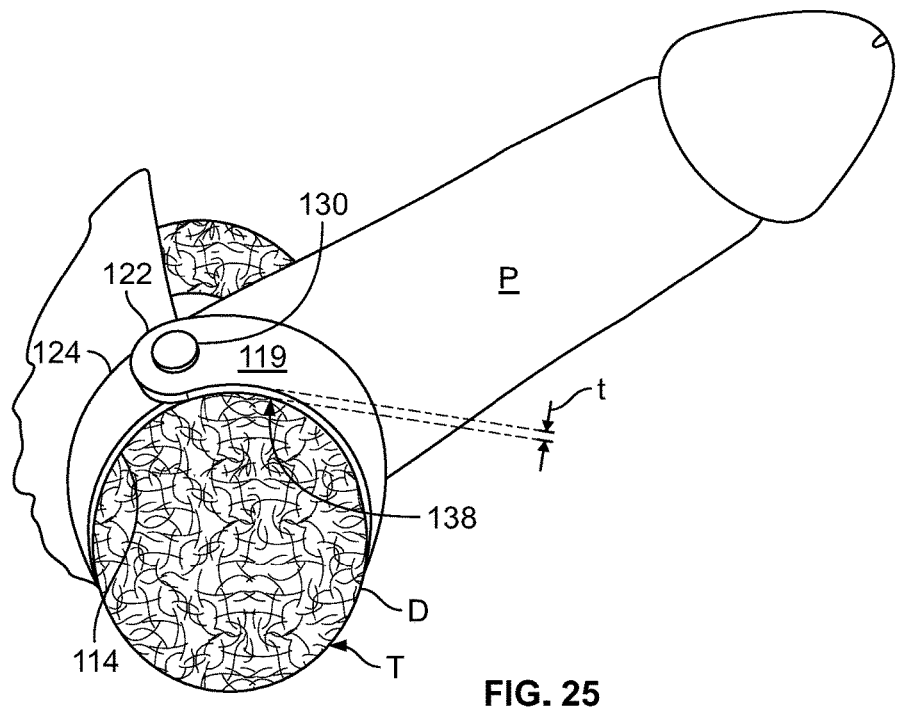
FIG. 25 is a side elevation view of the scrotal loop restraint of FIG. 22 in a donned state.

A manner of donning loop restraint 108 is illustrated in FIGS. 23-25. First, midsection 118 is positioned below testicles T, with inner face 117 facing upward and left and right sides 110, 114 of restraint body 109 aligned with those of penis P. Rear right and left flaps 124, 126 are then turned inwardly over the top of testicles T, as shown in FIG. 23. Right and left male snaps 132 and 134, disposed on outer face 119 at flaps 124, 126, are thus turned to face up, and the respective female snaps 130, 128 are connected thereto by turning the respective front right and left flaps 122, 120 inwardly over testicles T to align the corresponding snaps. In this manner, a portion of each of left side 110 and right side 114 is formed into a left-hand or right-hand loop defining a respective left opening 136 and right opening 138, with a restrained portion of the respective testicle T, disposed to a lower/lateral side of the opening 136, 138, the opening 136, 138 being of a size and shape that prevents the passage of at least a major (e.g., largest and/or widest) cross section D of the restrained portion of testicle T therethrough in a medial/upward direction toward the male's abdominal cavity, as illustrated in FIGS. 24 and 25.

With reference to FIG. 24, it will be appreciated that testicles T may be kept apart from each other by a mediolateral center-to-center separation distance d between their respective sections D when loop restraint 108 is worn. Separation distance d may be significantly greater than a distance by which testicles T would be separated without intervention, whether in repose or in a partially or fully retracted state. Provided sufficient stiffness of body 109 to resist collapse or bending in the mediolateral dimension, which may depend, for example, on its material composition, thickness t (shown in FIG. 25, which may desirably be no greater than about ¼ in, to fit easily, for example, in a typical wallet or clothing pocket, whether in a collapsed/folded or expanded/unfolded state), width w, and/or other dimensions, separation distance d may be maintained by midsection 118 of restraint 108 acting as a spacer between testicles T. Thus, separation distance d may in part be a function of width w. Inherently, keeping testicles T laterally spaced apart also keeps either testicle T from retracting into the abdominal cavity. For one, the opening into which each testicle T would retract absent intervention is relatively centrally located, so that testicle T cannot enter the abdomen from a laterally displaced position imposed by loop restraint 108. In addition, the vas deferens tends to retract ahead of the testicle into the abdomen, and the vas deferens is attached to each testicle T on the medial (inner) side of the respective opening 136, 138. Thus, once testicle T abuts the respective lateral side 110, 114 of loop restraint 108 adjacent the respective opening 136, 138, neither the vas deferens nor testicle T can continue to retract medially, though the retraction response may have the effect of raising testicles T and loop restraint together vertically until the latter abuts the underside of penis P, as shown in FIG. 25, the shape of which may be accommodated by the concave contour of front side 112, best seen in FIG. 22.

Figure 26:
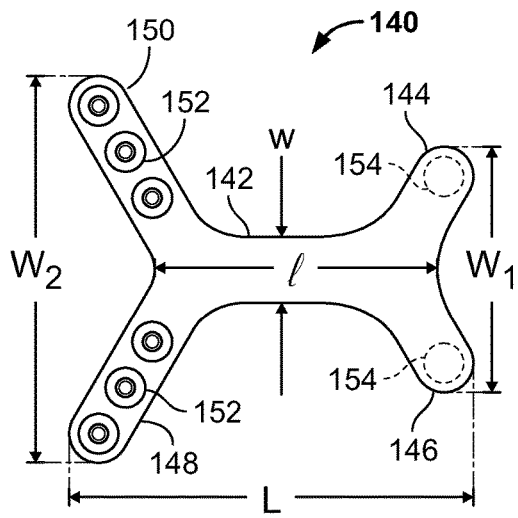
FIG. 26 is a top plan view of a scrotal loop restraint according to an aspect of the invention.
Figure 27:
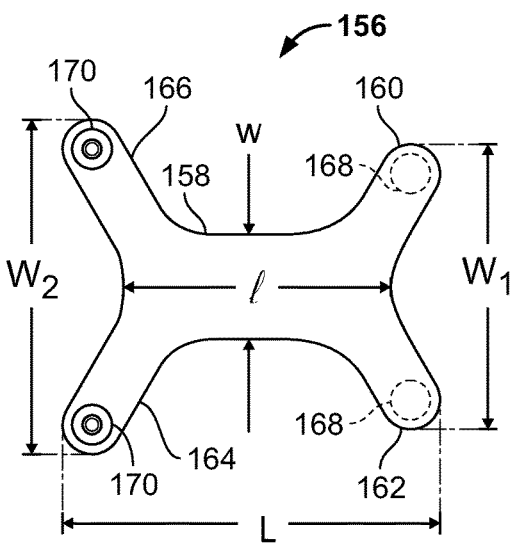
FIG. 27 is a top plan view of a scrotal loop restraint according to an aspect of the invention.
Figure 28:
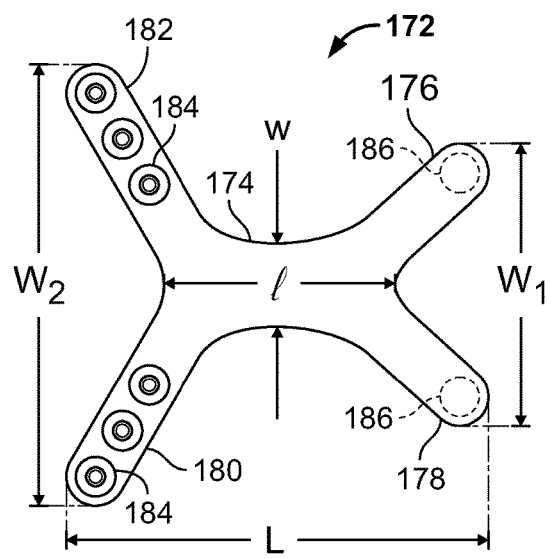
FIG. 28 is a top plan view of a scrotal loop restraint according to an aspect of the invention.
Figure 29:
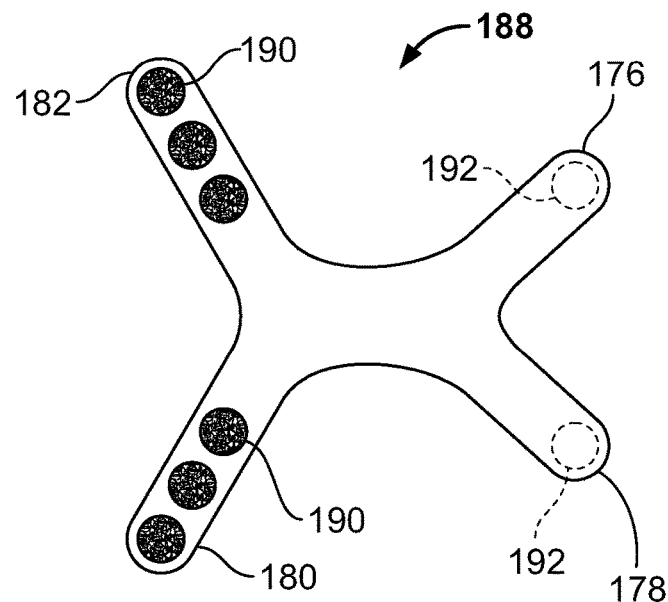
FIG. 29 is a top plan view of a scrotal loop restraint according to an aspect of the invention.
Figure 30:
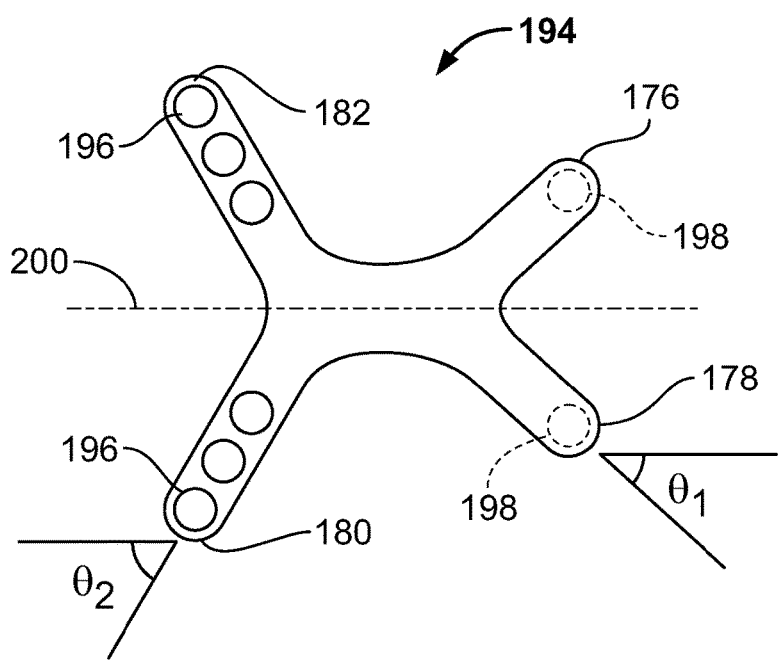
FIG. 30 is a top plan view of a scrotal loop restraint according to an aspect of the invention.

Referring to FIGS. 26-30, some of the many possible variations on a loop restraint according to the invention are illustrated, including three different body profile shapes, shown in FIGS. 26-28, and for the body profile shape shown in FIG. 28, three different closure types, shown in FIGS. 28-30.

Turning to FIG. 26, a loop restraint 140 having a body 142 exhibiting a first profile shape is shown. A minor width w, major front width W1, major rear width W2, minor length l, and major length L of body 142 are indicated. A front-left flap 144 and front-right flap 146 are significantly shorter than a rear-right flap 148 and rear-left flap 150 of body 142. The extra length of each rear flap 148, 150 can accommodate a plurality of snaps 152. For adjustment to a desired size, a selected one of snaps 152 may thus be mated with a snap 154 of the corresponding front flap 146, 144.

Turning to FIG. 27, a loop restraint 156 having a body 158 exhibiting a second profile shape is shown. A minor width w, major front width W1, major rear width W2, minor length l, and major length L of body 158 are indicated. A front-left flap 160 and front-right flap 162 are closer in size to a rear-right flap 164 and rear-left flap 166 of body 158, so that loop restraint 156 may have a more compact overall shape than that of loop restraint 140. Loop restraint 156 is illustrated as single-size, each front flap 160, 162 including a single snap 168 and each rear flap 164, 166 including a single snap 170. Alternatively, front and rear flaps of roughly equal length may each include a plurality of snaps, such as two snaps each, which may provide a comparable range of adjustability to that of loop restraint 140 in a more compact shape. Loop restraint 156 also differs from loop restraint 140 in other characteristic dimensions, notably including its significantly wider minor width w, which may promote a wider separation distance d between testicles T as described above.

Turning to FIG. 28, a loop restraint 172 having a body 174 exhibiting a second profile shape is shown. A minor width w, major front width W1, major rear width W2, minor length l, and major length L of body 174 are indicated. As in body 142 of loop restraint 140, a front-left flap 176 and front-right flap 178 are significantly shorter than a rear-right flap 180 and rear-left flap 182 of body 174, the extra length of each rear flap 180, 182 accommodating a plurality of snaps 184, a selected one of which may be mated with a snap 186 of the corresponding front flap 176, 178. Loop restraint 172 also has a proportionally similar minor width w to that of loop restraint 140, but a substantially smaller minor length l, while a greater portion of its major length L is comprised in the lengths of its flaps, and a lesser portion in the length of its longitudinal midsection. The relatively small midsection dimensions l, w and relatively long flaps 176, 178, 180, 182 of loop restraint 172 may permit a greater number and/or wider spacing of snaps 184, while also saving material compared to shapes with larger midsection dimensions l, w.

With reference to FIG. 29, a loop restraint 188 is illustrated, which has the same body 174 and flaps 176, 178, 180, 182 as loop restraint 172, with a hook-and-loop closure system in place of snaps. Each rear flap 180, 182 includes a plurality of loop pile patches 190, a selected one of which may mate with a hook patch 192 of the corresponding front flap 178, 176. Loop pile patches 190 may alternatively be a single elongate loop pile patch, with the benefits of continuous adjustability and simplified construction. On the other hand, discrete loop pile patches 190 provide the benefit of a visual indicator of a discrete size adjustment, facilitating the selection of a same (or different) size adjustment on each side, or in subsequent uses.

Turning to FIG. 30, a loop restraint 194 is illustrated, which has the same body 174 and flaps 176, 178, 180, 182 as loop restraint 172, with magnetic connectors in place of snaps. Each rear flap 180, 182 includes a plurality of magnetic connectors 196, configured for mating a selected one of magnetic connectors 196 with a magnetic connector 198 of the corresponding front flap 178, 176. Magnetic connectors 198 are preferably magnets, while magnetic connectors 196 may be magnets or other magnetically attracted bodies.

Also indicated in FIG. 30 are characteristic angles theta1 of front-right flap 178, and theta2 of rear-right flap 180, relative to a longitudinal axis 200 of body 174. A front flap angle, such as angle theta1, and a rear flap angle, such as angle theta2, are typically the same for both sides of a loop restraint according to the invention, though sides may differ in custom or alternative models, to accommodate the anatomical asymmetry of an individual male or varying degrees of anatomical asymmetry observed in the male population, as noted previously. Other desired shape features of loop restraints not labeled in the drawing figures may include a width or range of widths of each flap, which, though varying along their respective lengths, may desirably be in a range of about 0.25 in to about 0.75 in for a substantial portion thereof; a central radius of curvature of a front side, which may advantageously be selected to conform to the underside of an erect penis shaft when worn; and a central radius of curvature of a rear side, which may advantageously be selected to conform to the rear/underside of a rear portion of the scrotum when worn.

Many variations on loop restraints according to the invention are possible within the scope of the invention. For example, instead of flexible flaps detachably connecting to form a loop, each loop may be an elastic band defining an opening of a desired size when in a relaxed state, and the loop may be stretched open to receive each testicle, and then released once a section of the testicle has been inserted through the loop that will not be able to pass back through the relaxed loop. Whether the loops are elastic or manually closable, a stiff or rigid connecting member of a different material may be connected between the loops to maintain a desired separation distance between the loops, and thus the testicles. Alternatively, the loops may be manually closable but formed of two rigid, pivotally connected halves.

A variety of materials may be suitable for constructing loop testicular retraction restraints ("loop restraints" or "loop type restraints") according to the above-described embodiments or other embodiments of the invention. For example, the body may be formed from a polymer (e.g., silicone or other suitable elastomer), leather, fabric material (which may be thickened or otherwise reinforced against medial collapse or bending in a lateral midsection, such as by inclusion of another material), or any other flexible, durable material that can be comfortably held against the skin of the scrotum and can be used to form a closable loop restraint of appropriate dimensions. Closures may be snaps, hook-and-loop fasteners, or any other type of closure that may be readily fastened and opened manually. In embodiments with magnetic closures, each coordinating pair of magnetic elements may include two magnets or one magnet and a corresponding magnetically attracted body.

Other Variations

While the invention has been described with respect to certain embodiments, as will be appreciated by those skilled in the art, it is to be understood that the invention is capable of numerous changes, modifications and rearrangements, and such changes, modifications and rearrangements are intended to be covered by the following claims.

What is claimed is:

1. A human testicular retraction restraint, comprising
   a broad and thin body of flexible material having a left-hand loop at a left side and a right-hand loop at a right side;
   each of the left-hand loop and right-hand loop comprising a flexible member having spaced apart closure portions manually movable into and away from proximity, the closure portions being manually attachable to close the respective loop and manually detachable to open the respective loop.

2. The restraint of claim 1, the closure portions being selected from the group consisting of snaps, hook-and-loop fasteners, and magnetic couplings.

3. A method of restraining human testicular retraction using a restraint comprising a first clip member operative to be disposed against a first area of a man's scrotum between the testicles; a second clip member operative to be disposed against a second area of the scrotum opposite the first area; a biasing mechanism operative to produce a gripping force to urge the first and second clip members toward each other in a gripping direction to grip a portion of the scrotum between the first and second areas and to suspend the restraint from the gripped portion of the scrotum; a right-hand obstructing feature comprising a rightwardly extending portion of at least one of the first clip member and the second clip member; and a left-hand obstructing feature comprising leftwardly extending portion of at least one of the first clip member and the second clip member; the method comprising
   prior to a man's sexual climax, gripping the portion of the scrotum between the clip members such that the right-hand obstructing feature is disposed between the man's right testicle and abdomen and the left-hand obstructing feature is disposed between the man's left testicle and abdomen.

4. The method of claim 3, the first and second clip members being connected at a pivotal joint operative to be disposed approximately at a lower end of the restraint when the restraint is worn.

5. The method of claim 4, the pivotal joint comprising a strip of flexible material.

6. The method of claim 3, the first clip member comprising a first gripping surface operative to be disposed against said first scrotum area, the second clip member comprising a second gripping surface operative to be disposed against said second scrotum area, an overlapping region of the first and second gripping surfaces defining a gripping area, a size of the gripping area being in a range from about 2 in$^2$ to about 7 in$^2$.

7. The method of claim 3, each of the first and second clip members having a thickness in the gripping direction no greater than about ¼ inch.

8. The method of claim 3, the first and second clip members having a combined thickness in the gripping direction no greater than about ½ inch.

9. The method of claim 3, a profile of the restraint in a plane normal to the gripping direction lying within an approximately 3.5-in by 2-in rectangle.

10. The method of claim 3, the right-hand obstructing feature comprising at least a portion of a right side of at least one of the first and second clip members that tapers to the right toward an upper end of the right side, and the left-hand obstructing feature comprising at least a portion of the left side of at least one of the first and second clip members that tapers to the left toward an upper end of the left side.

11. The method of claim 3, the biasing mechanism comprising a magnet carried by at least one of the first and second clip members, and a magnetically attracted component carried by the other clip member.

12. The method of claim 3, further comprising an engaging surface of at least one of the first and second clip members operative to resist downward sliding of the engaging surface against the respective first or second area of the man's scrotum.

\* \* \* \* \*